(12) United States Patent
Jennings et al.

(10) Patent No.: US 9,072,833 B2
(45) Date of Patent: Jul. 7, 2015

(54) INJECTION DEVICE

(75) Inventors: Douglas Ivan Jennings, Royston (GB); Joseph Peter Corrigan, Cambridge (GB); Timothy Donald Barrow-Williams, St Albans (GB); Matthew James Brady, Cambs (GB)

(73) Assignee: Cilag GMBH International, Landis & Gyrstrasse (CH)

( * ) Notice: Subject to any disclaimer, the term of this patent is extended or adjusted under 35 U.S.C. 154(b) by 738 days.

(21) Appl. No.: 12/301,475

(22) PCT Filed: May 29, 2007

(86) PCT No.: PCT/GB2007/001973
§ 371 (c)(1),
(2), (4) Date: Oct. 8, 2009

(87) PCT Pub. No.: WO2007/138299
PCT Pub. Date: Dec. 6, 2007

(65) Prior Publication Data
US 2010/0016793 A1    Jan. 21, 2010

(30) Foreign Application Priority Data

Jun. 1, 2006 (GB) .................................. 0610854.2

(51) Int. Cl.
*A61M 5/20* (2006.01)
*A61M 5/32* (2006.01)

(52) U.S. Cl.
CPC ............ *A61M 5/2033* (2013.01); *A61M 5/3202* (2013.01); *A61M 5/3204* (2013.01); *A61M 5/326* (2013.01); *A61M 2005/208* (2013.01); *A61M 2005/206* (2013.01)

(58) Field of Classification Search
CPC ............ A61M 5/2033; A61M 5/3202; A61M 2005/208; A61M 5/326; A61M 5/3287; A61M 5/3204; A61M 2005/206

USPC .................... 604/192, 263, 163, 68, 198, 195
See application file for complete search history.

(56) References Cited

U.S. PATENT DOCUMENTS

| 1,845,036 A | 2/1932 | Busher |
| 2,019,382 A | 10/1935 | Aronson |

(Continued)

FOREIGN PATENT DOCUMENTS

| CH | 518102 A | 1/1972 |
| CN | 2059579 U | 7/1990 |

(Continued)

OTHER PUBLICATIONS

International Search Report dated Sep. 5, 2005; International Application No. PCT/GB2005/002117.

(Continued)

*Primary Examiner* — Nicholas Lucchesi
*Assistant Examiner* — Weng Lee

(57) ABSTRACT

An injection device 110 is described having a housing 112 that receives a syringe 114 having a needle 118, wherein the syringe is supported in a syringe carrier 150. The injection device 110 has a removable cap 190. The syringe 114 and syringe carrier 150 are biased by a return spring 126 from an extended position in which the needle 118 extends from the housing 112 through an exit aperture 128 to a retracted position in which it does not. The syringe carrier 150 abuts a surface inside the removable cap 190 which prevents forward movement of the syringe carrier 150 when the cap is in place. The injection device is less prone to failure than prior art devices and is safer should failure occur.

8 Claims, 4 Drawing Sheets

(56) References Cited

U.S. PATENT DOCUMENTS

| | | | |
|---|---|---|---|
| 2,531,267 A | 11/1950 | Harisch | |
| 2,764,977 A | 10/1956 | Ferguson | |
| 2,828,742 A | 4/1958 | Ashkenaz | |
| 3,131,692 A | 5/1964 | Love | |
| 3,320,955 A | 5/1967 | Sarnoff | |
| 3,329,146 A | 7/1967 | Waldman | |
| 3,543,603 A | 12/1970 | Gley | |
| 3,656,472 A | 4/1972 | Moura | |
| 3,702,608 A | 11/1972 | Tibbs | |
| 3,742,948 A | 7/1973 | Post et al. | |
| 3,797,488 A | 3/1974 | Hurschman et al. | |
| 3,797,489 A | 3/1974 | Sarnoff | |
| 3,880,163 A | 4/1975 | Ritterskamp | |
| 3,976,069 A | 8/1976 | Ong | |
| 4,165,739 A | 8/1979 | Doherty et al. | |
| 4,180,070 A | 12/1979 | Genese | |
| 4,185,628 A | 1/1980 | Kopfer | |
| 4,194,505 A | 3/1980 | Schmitz | |
| 4,222,380 A | 9/1980 | Terayama | |
| 4,231,368 A | 11/1980 | Becker | |
| 4,236,516 A | 12/1980 | Nilson | |
| 4,299,238 A | 11/1981 | Baidwan et al. | |
| 4,333,459 A | 6/1982 | Becker | |
| 4,378,015 A | 3/1983 | Wardlaw | |
| 4,394,863 A | 7/1983 | Bartner | |
| 4,403,989 A | 9/1983 | Christensen et al. | |
| 4,407,283 A | 10/1983 | Reynolds | |
| 4,425,120 A | 1/1984 | Sampson et al. | |
| 4,430,082 A | 2/1984 | Schwabacher | |
| 4,521,237 A | 6/1985 | Logothetis | |
| 4,561,856 A | 12/1985 | Cochran et al. | |
| 4,636,201 A | 1/1987 | Ambrose et al. | |
| 4,639,250 A | 1/1987 | Rycroft | |
| 4,642,099 A | 2/1987 | Phillips et al. | |
| 4,676,530 A | 6/1987 | Nordgren et al. | |
| 4,744,786 A | 5/1988 | Hooven et al. | |
| 4,787,891 A | 11/1988 | Levin et al. | |
| 4,874,383 A | 10/1989 | McNaughton | |
| 4,874,384 A | 10/1989 | Nunez | |
| 4,929,232 A | 5/1990 | Sweeney et al. | |
| 4,969,870 A | 11/1990 | Kramer et al. | |
| 4,988,339 A | 1/1991 | Vadher | |
| 5,009,646 A | 4/1991 | Sudo et al. | |
| 5,026,349 A | 6/1991 | Schmitz et al. | |
| 5,057,079 A | 10/1991 | Tiemann et al. | |
| 5,092,842 A | 3/1992 | Bechtold et al. | |
| 5,098,400 A | 3/1992 | Crouse et al. | |
| 5,112,119 A | 5/1992 | Cooke et al. | |
| 5,114,406 A | 5/1992 | Gabriel et al. | |
| 5,122,119 A | 6/1992 | Lucas | |
| 5,137,516 A | 8/1992 | Rand et al. | |
| 5,141,496 A | 8/1992 | Dalto et al. | |
| 5,147,325 A * | 9/1992 | Mitchell et al. | 604/192 |
| 5,156,599 A | 10/1992 | Ranford et al. | |
| 5,176,643 A | 1/1993 | Kramer et al. | |
| 5,190,526 A | 3/1993 | Murray et al. | |
| 5,242,416 A | 9/1993 | Hutson | |
| 5,250,026 A | 10/1993 | Ehrlich et al. | |
| 5,250,037 A | 10/1993 | Bitdinger | |
| 5,263,933 A | 11/1993 | Novacek et al. | |
| 5,267,963 A | 12/1993 | Bachynsky | |
| 5,271,744 A | 12/1993 | Kramer et al. | |
| 5,295,965 A | 3/1994 | Wilmot | |
| 5,300,030 A | 4/1994 | Crossman et al. | |
| 5,312,364 A | 5/1994 | Jacobs | |
| 5,330,081 A | 7/1994 | Davenport | |
| 5,330,430 A | 7/1994 | Sullivan | |
| 5,358,489 A | 10/1994 | Wyrick | |
| 5,364,369 A | 11/1994 | Reynolds | |
| 5,368,577 A | 11/1994 | Teoh et al. | |
| 5,372,586 A | 12/1994 | Haber et al. | |
| 5,391,151 A | 2/1995 | Wilmot | |
| 5,405,362 A | 4/1995 | Kramer et al. | |
| 5,411,488 A | 5/1995 | Pagay et al. | |
| 5,425,715 A | 6/1995 | Dalling et al. | |
| 5,451,210 A | 9/1995 | Kramer et al. | |
| 5,478,316 A * | 12/1995 | Bitdinger et al. | 604/135 |
| 5,480,387 A | 1/1996 | Gabriel et al. | |
| 5,487,732 A | 1/1996 | Jeffrey | |
| 5,489,256 A | 2/1996 | Adair | |
| 5,503,627 A | 4/1996 | McKinnon et al. | |
| 5,514,097 A | 5/1996 | Knauer | |
| 5,520,653 A | 5/1996 | Reilly et al. | |
| 5,540,660 A | 7/1996 | Jenson et al. | |
| 5,540,666 A | 7/1996 | Barta et al. | |
| 5,540,709 A | 7/1996 | Ramel et al. | |
| 5,567,160 A | 10/1996 | Massino | |
| 5,569,191 A | 10/1996 | Meyer | |
| 5,569,192 A | 10/1996 | van der Wal | |
| 5,575,777 A | 11/1996 | Cover et al. | |
| 5,599,302 A | 2/1997 | Lilley et al. | |
| 5,599,309 A | 2/1997 | Marshall et al. | |
| 5,607,395 A | 3/1997 | Ragsdale et al. | |
| 5,609,577 A | 3/1997 | Haber et al. | |
| 5,609,584 A | 3/1997 | Gettig et al. | |
| 5,611,785 A | 3/1997 | Mito et al. | |
| 5,637,094 A | 6/1997 | Stewart, Jr. et al. | |
| 5,645,536 A | 7/1997 | Whisson | |
| 5,647,845 A | 7/1997 | Haber et al. | |
| 5,649,912 A | 7/1997 | Peterson | |
| 5,658,259 A | 8/1997 | Pearson et al. | |
| 5,665,071 A | 9/1997 | Wyrick | |
| 5,681,291 A | 10/1997 | Galli | |
| 5,697,908 A | 12/1997 | Imbert | |
| 5,702,367 A | 12/1997 | Cover et al. | |
| 5,704,911 A | 1/1998 | Parsons et al. | |
| 5,709,662 A | 1/1998 | Olive et al. | |
| 5,713,866 A | 2/1998 | Wilmot | |
| 5,748,316 A | 5/1998 | Wakabayashi et al. | |
| 5,779,668 A | 7/1998 | Grabenkort | |
| 5,779,677 A | 7/1998 | Frezza | |
| 5,807,334 A | 9/1998 | Hodosh et al. | |
| 5,817,058 A | 10/1998 | Shaw | |
| 5,827,262 A | 10/1998 | Neftel et al. | |
| 5,843,036 A | 12/1998 | Olive et al. | |
| 5,855,839 A | 1/1999 | Brunel | |
| 5,865,795 A | 2/1999 | Schiff et al. | |
| 5,865,804 A | 2/1999 | Bachynsky | |
| 5,868,711 A | 2/1999 | Kramer et al. | |
| 5,879,327 A | 3/1999 | Moreau DeFarges et al. | |
| 5,913,843 A | 6/1999 | Jentzen | |
| 5,928,205 A | 7/1999 | Marshall | |
| 5,954,738 A | 9/1999 | LeVaughn et al. | |
| 5,957,897 A | 9/1999 | Jeffrey | |
| 5,960,797 A | 10/1999 | Kramer et al. | |
| 5,997,513 A | 12/1999 | Smith et al. | |
| 6,007,515 A | 12/1999 | Epstein et al. | |
| 6,015,438 A | 1/2000 | Shaw | |
| 6,017,330 A | 1/2000 | Hitchins et al. | |
| 6,036,675 A | 3/2000 | Thorne et al. | |
| 6,045,534 A | 4/2000 | Jacobsen et al. | |
| 6,068,614 A | 5/2000 | Kimber et al. | |
| 6,077,247 A | 6/2000 | Marshall et al. | |
| 6,083,197 A | 7/2000 | Umbaugh | |
| 6,086,562 A | 7/2000 | Jacobsen et al. | |
| 6,090,070 A | 7/2000 | Hager et al. | |
| 6,090,078 A | 7/2000 | Erskine | |
| 6,090,897 A | 7/2000 | Akasaki et al. | |
| 6,099,503 A | 8/2000 | Stradella | |
| 6,099,504 A | 8/2000 | Gross | |
| 6,123,684 A | 9/2000 | Deboer et al. | |
| 6,139,534 A | 10/2000 | Niedospial, Jr. et al. | |
| 6,159,161 A | 12/2000 | Hodosh | |
| 6,159,181 A | 12/2000 | Crossman et al. | |
| 6,159,184 A | 12/2000 | Perez et al. | |
| 6,162,199 A | 12/2000 | Geringer | |
| 6,171,276 B1 | 1/2001 | Lippe et al. | |
| 6,179,812 B1 | 1/2001 | Botich et al. | |
| 6,186,980 B1 | 2/2001 | Brunel | |
| 6,190,363 B1 | 2/2001 | Gabbard et al. | |
| 6,193,696 B1 | 2/2001 | Jansen et al. | |
| 6,203,530 B1 | 3/2001 | Stewart, Sr. | |
| 6,209,738 B1 | 4/2001 | Jansen et al. | |
| 6,221,044 B1 | 4/2001 | Grecco | |

(56) References Cited

U.S. PATENT DOCUMENTS

| | | |
|---|---|---|
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 * | 6/2006 | Crossman et al. ............ 604/110 |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,491,530 B2 | 7/2013 | Maritan |
| 8,696,628 B2 | 4/2014 | Grunhut |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron Luc et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |

(56) References Cited

U.S. PATENT DOCUMENTS

| | | |
|---|---|---|
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1* | 5/2005 | Brunnberg ............. 604/197 |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1* | 9/2005 | Hommann et al. ........ 604/240 |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1* | 2/2006 | Rimlinger et al. ........ 604/198 |
| 2006/0036217 A1* | 2/2006 | Doyle ................. 604/198 |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |

(56) References Cited

FOREIGN PATENT DOCUMENTS

| | | |
|---|---|---|
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 1932558 A1 | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| JP | 59-115053 A | 7/1984 |
| JP | 2-185261 A | 7/1990 |
| JP | 2-502971 T | 9/1990 |
| JP | 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/08725 | 11/1988 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 | 2/2003 |
| WO | WO 03/015846 A2 | 2/2003 |
| WO | WO 03/015853 A1 | 2/2003 |
| WO | WO 03/039633 A2 | 5/2003 |

(56) References Cited

FOREIGN PATENT DOCUMENTS

| | | |
|---|---|---|
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 2006081640.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.

(56) References Cited

OTHER PUBLICATIONS

International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11163779.9.
Singapore Search Report dated Mar. 15, 2012; Application No. SG 201007017-5.
European Search Report dated Aug. 3, 2011; Application No. 11170040.7.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
Great Britain Search Report dated Sep. 25, 2008; Application No. GB0811348.2.
European Search Report dated Oct. 15, 2013; Application No. 12182553.3.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
International Search Report dated Sep. 9, 2014; International Application No. PCT/EP2014/062168.
Great Britain Search Report dated Dec. 10, 2013; Application No. GB1310393.2.
Great Britain Search Report dated Dec. 10, 2013; Application No. GB1310372.6.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Jan. 29, 2015; International Application No. PCT/EP2014/062167.
International Search Report dated Sep. 8, 2014; International Application No. PCT/EP2014/062162.
International Search Report dated Sep. 16, 2014; International Application No. PCT/EP2014/062160.

* cited by examiner

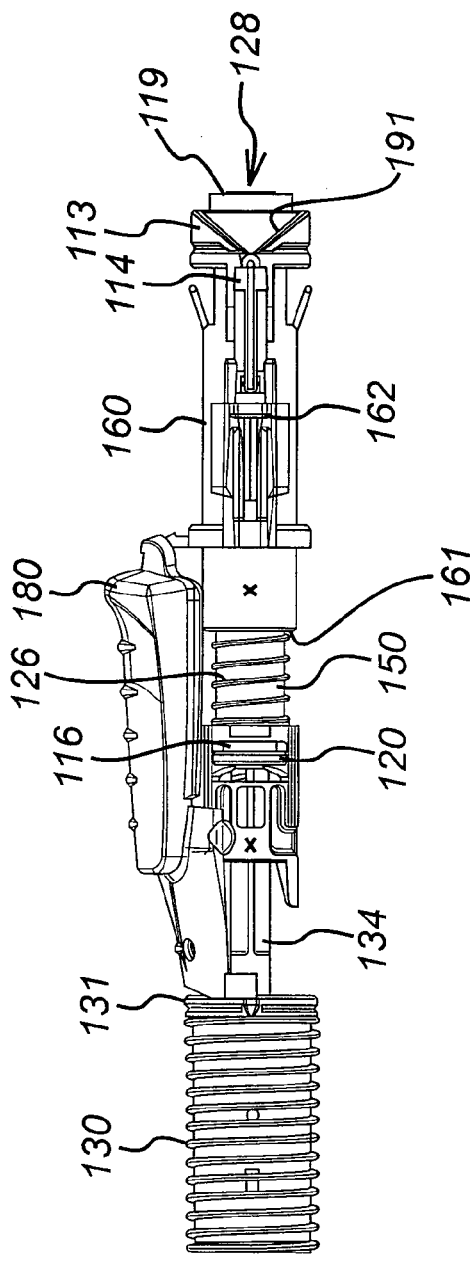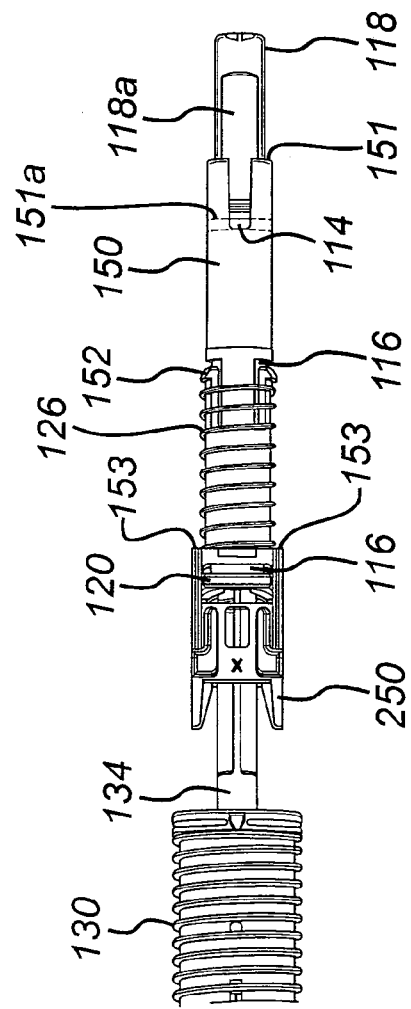
FIG. 2a
FIG. 2b

INJECTION DEVICE

FIELD OF THE INVENTION

The present invention relates to an injection device of the type that receives a syringe, extends it, discharges its contents and then retracts it automatically.

BACKGROUND OF THE INVENTION

Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Often, such injection devices are required to work with glass pre-filled syringes that were originally designed for manual use. Such glass syringes have a flange at their base to allow a user to grip the syringe. The substantial force produced by the drive spring is applied to the piston of the syringe. This force is transferred to the housing and return spring, via syringe carrier. The syringe carrier is normally sheath which is designed to envelop the syringe and take up forces applied to the syringe to prevent damage to the frangible glass body of the syringe.

The syringe is manufactured with a boot which covers its needle. The aim of the boot is to protect the needle and maintain its sterility. The needle is joined to the glass body of the syringe by an integrity seal. With injection devices of the present invention, the syringe boot may be connected to the syringe body via a frangible connection, or, alternatively, the boot may be a tight rubber boot covering the needle. In either case, the boot is gripped by a cap of the injection device so that the boot becomes removed when the cap of the injection device is removed prior to use.

In current injection devices, the syringe carrier is nominally biased into the syringe by a return spring. The bias is only overcome when a drive spring is released which forces the syringe carrier against the bias of the return spring to move the syringe into an extended position whilst its contents is ejected. However, before actuation of the drive spring, the syringe carrier is still free to move against the return spring when high loading forces are applied externally to the injection device, for example during impact of the injection device with a hard surface, such as when the device is dropped. In such situations, since the boot is held rigidly in the cap of the injection device, movement of the syringe carrier (and syringe) may disturb the integrity of the needle seal with the syringe or cause the frangible connection between the boot and the syringe to break. Of course, this exposes the needle and its contents to a non-sterile environment which is undesirable.

SUMMARY OF THE INVENTION

The injection devices of the present invention are designed to deal with the aforementioned problems.

An injection device according to the present invention comprises:
- a housing adapted to receive a syringe having a reservoir portion and a discharge nozzle, so that the syringe is movable between a retracted position in which the discharge nozzle is contained within the housing and an extended position in which the discharge nozzle extends from the housing through an exit aperture;
- a drive that acts upon the syringe to advance it from its retracted position to its extended position and discharge its contents through the discharge nozzle;
- a removable cap adapted to be connected to the housing for closing the exit aperture; and
- a syringe carrier for carrying the syringe as it is advanced, wherein the removable cap is adapted to restrict movement of the syringe carrier in a direction towards the exit aperture when the removable cap is connected to the housing.

In this way, the syringe carrier, and, hence syringe is prevented from being moved when an excessive impact force is applied to the syringe.

Preferably, the cap provides a first interface for restricting movement of the syringe carrier in a direction towards the exit aperture. The syringe carrier may provide a second interface for engaging the first interface. The first interface and second interface may each comprise a planar surface and the first interface may be located at an edge of on an annular component within the cap.

Preferably, the annular component is adapted to extend into the exit aperture when connected to the housing.

In a particular embodiment, the annular component is adapted to grip a removable shield on the discharge nozzle of the syringe.

In this way, the needle shield can be removed when the cap of the injection device is removed.

The syringe carrier may comprise a sheath for surrounding the reservoir portion of the syringe, wherein the sheath has a first internal diameter along its length, and an intermediate section with a second internal diameter which is smaller than the first internal diameter so that the intermediate section of the sheath is adapted to support the syringe between the reservoir portion and the discharge nozzle.

The second interface may be located on an annular protrusion at the first end of the syringe carrier which extends over the discharge nozzle. Preferably, the annular protrusion is a split annular protrusion. The injection device may further comprise: a sliding sleeve projecting from the exit aperture; and at least one locking arm which is engageable with the split annular protrusion, wherein the at least one locking arm disengages from the split annular protrusion on movement of the sliding sleeve into the injection device. In this way, engagement of the first and second interfaces when the cap is in place on the injection device prevents the locking arms of the device from being stressed during impact.

The annular protrusion may be split on diametrically opposing sides of the protrusion, and each split in the protrusion may comprise a locking surface for contacting with a corresponding locking arm. The injection device may further comprise means for biasing the syringe from its extended position to its retracted position.

The injection device may comprise a support for carrying the means for biasing the syringe.

BRIEF DESCRIPTION OF THE DRAWINGS

The invention will now be described by way of example with reference to the accompanying drawings, in which:

FIG. 2a shows an enlarged side view of part of the injection device shown in FIG. 1 without its external housing;

FIG. 2b shows an enlarged side view of part of the injection device shown in FIG. 1 without certain internal components of the injection device being shown;

DETAILED DESCRIPTION OF THE INVENTION

Figure 1A:
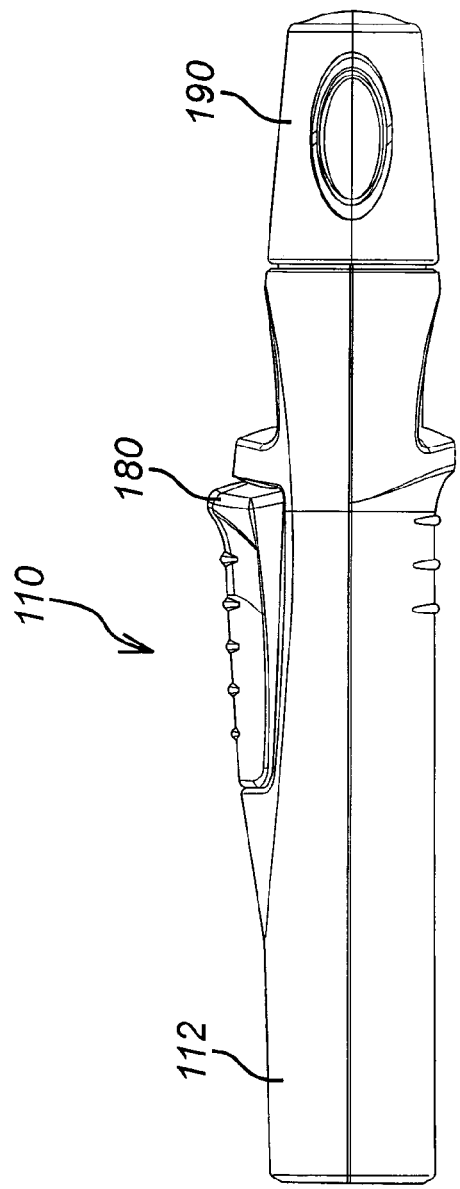
FIGS. 1a and 1b show a side view of an injection device according to the present invention.
Figure 1B:
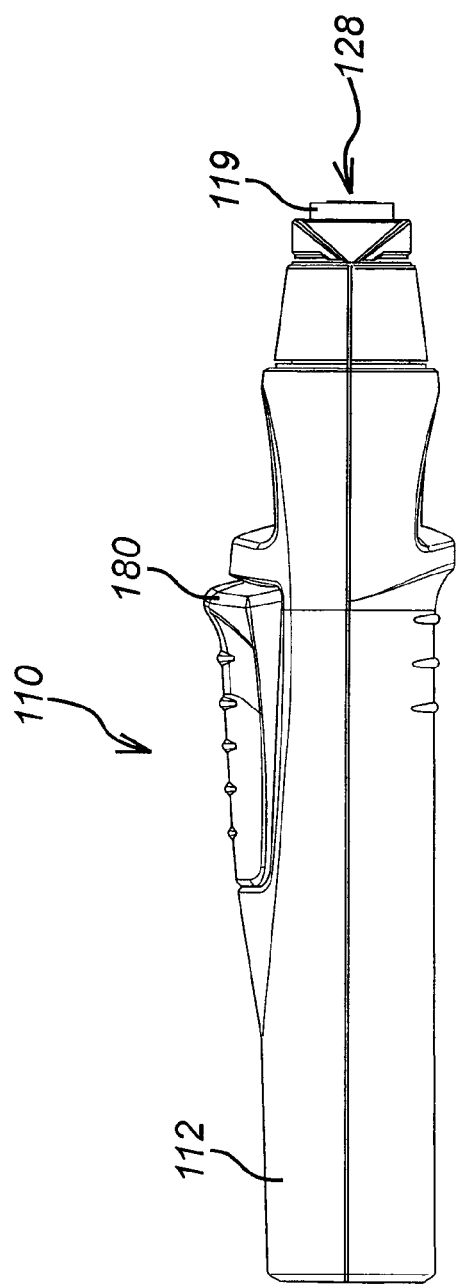

FIGS. 1a and 1b show an injection device 110, having an injection device housing 112. The injection device 110 has a removable cap 190. With the cap 190 removed, as shown in FIG. 2 the end of the housing 112 can be seen to have an exit aperture 128, through which the end of a sleeve 119 can emerge. The injection device 110 also has a trigger 180.

As shown in FIGS. 2a and 2b, the housing 112 contains a hypodermic syringe 114 of conventional type, including a syringe body 116 defining a reservoir and terminating at one end in a hypodermic needle (not shown) and at the other in a flange 120. The hypodermic needle is covered by a needle shield 118. The needle shield 118 is fixed inside the cap 190.

The syringe body 116 is of substantially constant diameter along the length of the reservoir, and is of significantly smaller diameter close to the end of the syringe which terminates in the hypodermic needle. A drive element 134 (syringe piston) acts through the bung of the syringe to discharge the contents of the syringe 114 through the needle 118. This drive element 134 constrains a drug (contained in the syringe) to be administered within the reservoir defined by syringe body 116. Whilst the syringe illustrated is of hypodermic type, this need not necessarily be so. Transcutaneous or ballistic dermal and subcutaneous syringes may also be used with the injection device of the present invention.

The housing 112 comprises a case nose 113 which is integrally formed with a sleeve 160. The sleeve 160 surrounds a syringe carrier 150 which is moveable within the sleeve 160 along its longitudinal axis.

As illustrated, the syringe 114 is housed within the syringe carrier 150. The syringe carrier 150 has a first end 151 and a reduced diameter section 151a. The section 151a of the syringe carrier supports the end of the syringe 114 nearest to the hypodermic needle. The syringe carrier 150 comprises a bearing surface 153 on which an end of a return spring 126 is located. The return spring 126, via the syringe carrier 150 biases the syringe 114 from an extended position in which the needle 118 extends from the aperture 128 in the housing 112 to a retracted position in which the needle 118 is contained within the housing 112.

If the syringe were to fail or break, the syringe carrier 150, which substantially surrounds the syringe 114 along its length, would contain the broken pieces of syringe and reduce the likelihood of them from escaping from the injection device.

The housing 112 also includes a trigger 180, and a drive which here takes the form of a compression drive spring 130. Drive from the drive spring 130 is transmitted via a multi-component drive (118a) to the drive element 134 of the syringe 114 to advance the syringe from its retracted position to its extended position and discharge its contents through the needle 118. The drive accomplishes this task by acting directly on the syringe 114 and the drug in the syringe. Static friction between the drive element 134 and the syringe body 116 initially ensures that both the syringe 114 and bung advance together, until the return spring 126 bottoms out when the bearing surface 153 on the syringe carrier 150 comes up against an opposing bearing surface 161 on the sleeve 160.

The trigger 180 is provided on the housing 112 remote from the exit aperture 128. The trigger, when operated, serves to decouple a drive sleeve 131 on which the drive spring 130 acts from the housing 112, allowing it to move relative to the housing 112 under the influence of the drive spring 130. The operation of the device is then as follows.

The cap 190 can be removed by a user with a twist and pull action or simply by pulling the cap. The exact action required depends on the type of syringe 114 being used. In one embodiment, the syringe 114 will comprise a rigid needle shield 118 containing a rubber boot (not shown) in which the needle is contained. In this embodiment, the needle shield 118 simply needs to be removed by pulling the cap 190 along the longitudinal axis of the device 110. In an alternative embodiment, the syringe 114 comprises a plastic needle shield 118 which is held to the syringe 114 by a frangible connection. In order to break the frangible connection, the cap 190 must be first twisted and then pulled along the longitudinal axis of the device 110. A guiding element 191 on the end cap 113 serves to guide the removal of the cap 190 in the way that is required to remove the needle shield 118.

Since the needle shield 118 is held inside the cap 190, removal of the cap 190, causes the needle shield to be removed, thereby exposing the needle of the syringe 114 within the injection device. At this time, the needle is still enclosed by the housing 112.

Initially, the syringe carrier 150 and syringe 114, are prevented from movement by a resilient latch member 162. By moving the sleeve 119 in a direction into the housing 112, the latch member 162 moves outwards disengaging from the syringe carrier 150. Once the latch member 162 has disengaged from the syringe carrier 150, the syringe 114 and syringe carrier 150 are free to move.

The trigger 180 can then be depressed by a user and the drive spring 130 is released. The drive spring 130 moves the drive sleeve 131, the piston 134 and, by virtue of static friction and hydrostatic forces acting through the drug to be administered, moves the syringe body 114 against the action of the return spring 126. The syringe body 114 moves the syringe carrier 150, which compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug begins to be discharged.

Figure 3:
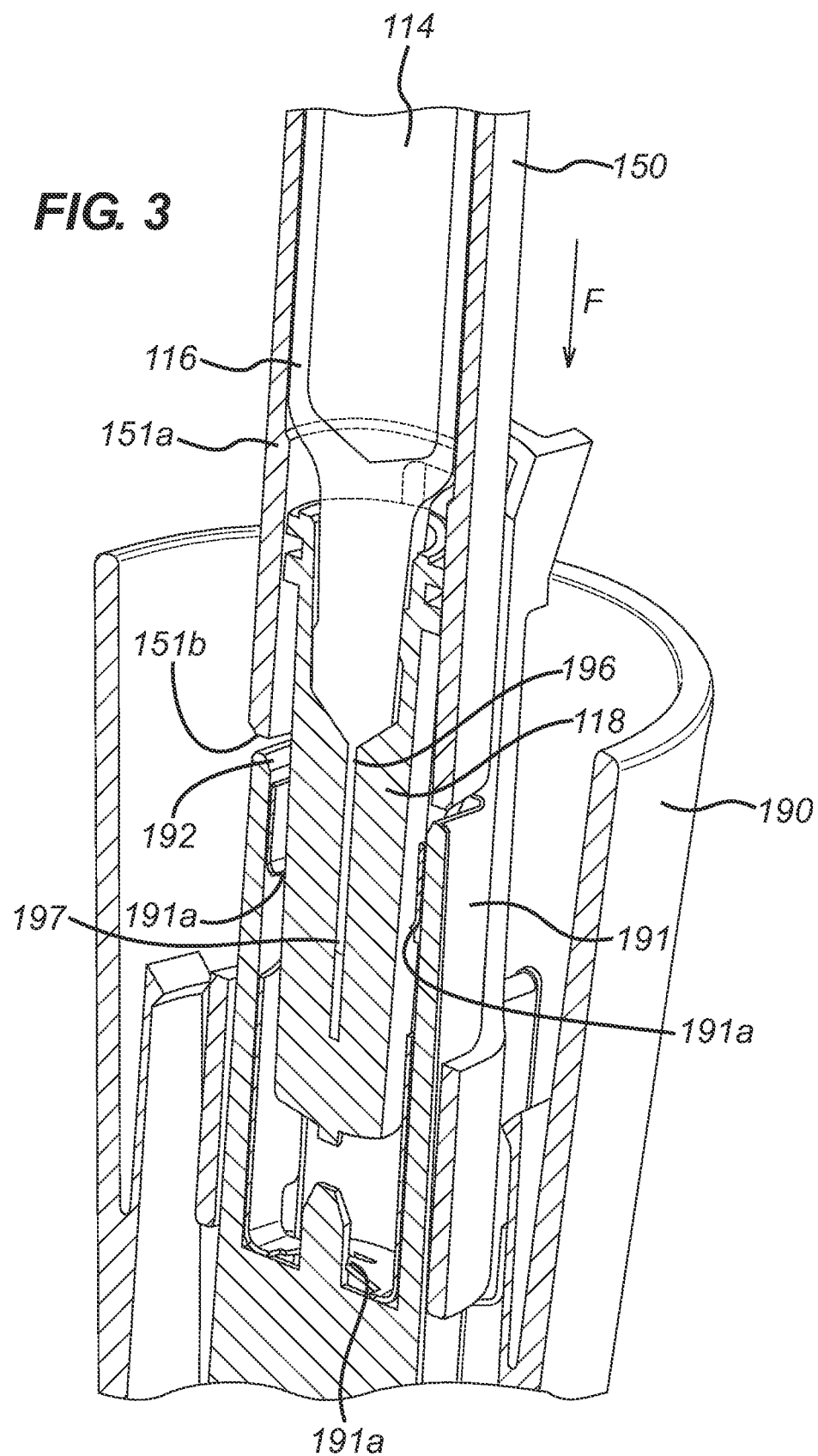
FIG. 3 shows a perspective cut-through view of the cap of the injection device according to the embodiment of FIG. 1.

The cap 190 of the injection device 110 of the present invention is depicted in FIG. 3. The cap 190 includes an annular protrusion 191 which extends into the exit aperture 128 when it is attached to the injection device 110.

The annular protrusion 191 includes grip means 191a which grip the boot 118 of the syringe 114 so that the boot is removed when the cap 190 is removed from the injection device 114.

At an end of the annular protrusion 191, where it opposes the exit aperture 128, there is an edge of the annular protrusion 191 which provides a first planar interface 192 for interfacing with the first end 151 of the syringe carrier 150, on which resides a second planar interface 151b. The annular protrusion 191 and syringe carrier 150 are dimensioned so that the first and second planar interfaces 192, 151b are in juxtaposition with each other when the cap 190 is in place on the injection device 110. Thus, when the cap 190 is in place, movement of the syringe carrier 150 in a direction F out of the injection device 110 is prevented, for example, when the injection device 110 experiences an external impact force, when it hits a hard surface. Since forward movement is inhibited, damage to an integrity seal 196 and/or needle 197 of the syringe is prevented.

The syringe carrier 150 is shown with an intermediate section 151a of reduced diameter which acts to prevent forward movement of the syringe 114 in the syringe carrier 150 by gripping the syringe 114 between the discharge nozzle and the syringe body 116.

Figure 4:
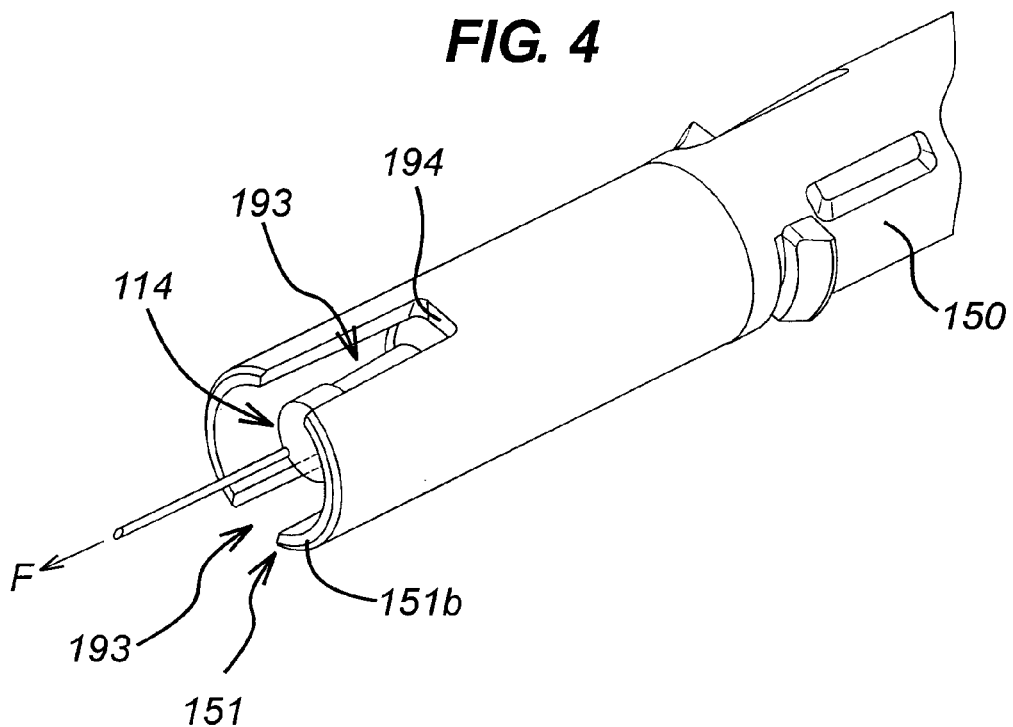
FIG. 4 shows a perspective view of the syringe carrier and syringe according to the embodiment of FIG. 1.

FIG. 4 shows the first end of the syringe carrier 150, on which the second planar interface 151b is located. The syringe carrier 150 is in the form of a split annular sheath, with a split 193 in each diametrically opposing side of the sheath at the first end 151 of the syringe carrier 150. Each split 193 provides a restraining interface 194. When the sleeve 119 is in its extended (unactuated) position, the resilient latch members 161 are in juxtaposition with the restraining interfaces 194, thereby preventing forward movement of the syringe carrier 150. When the sleeve 119 is pushed into the injection device 110, the latch members splay away from the syringe carrier 150, permitting the syringe carrier 150 to travel forward on actuation of the trigger 180.

When the cap 190 is in place on the injection device 110, juxtaposition of the interfaces 192 and 151b prevents loading of (and hence damage to) the latch members 161 during high loading of the impact of the injection device 110 with, for example, external forces.

Figure 5:
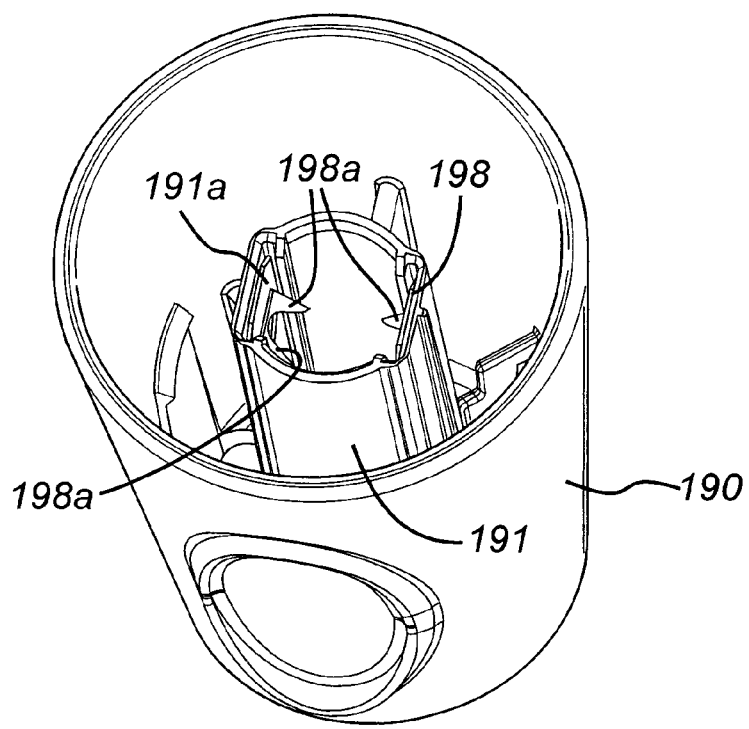
FIG. 5 shows a perspective view of the cap of the injection device according to the embodiment of FIG. 1.

FIG. 5 shows the cap 190 of the injection device as depicted in FIG. 3 without the boot 118 of the syringe 114 in place. The grip means 191a is seen to comprise rearward protrusions 198a which engage the boot 118 such that movement of the boot 118 in a direction out of the cap (i.e. opposite to direction F) is prevented. However, the grip means 191a is formed of resilient metallic material so that insertion of the boot 118 into the cap 190 is permitted, following which the protrusions engage the rubber material of the boot 118 to prevent its removal out of the cap 190.

It will of course be understood that the present invention has been described above purely by way of example and modifications of detail can be made within the scope of the invention.

The invention claimed is:

1. An injection device comprising:
   a housing adapted to receive a syringe having a reservoir portion and a discharge nozzle, so that the syringe is movable between a retracted position in which the discharge nozzle is contained within the housing and an extended position in which the discharge nozzle extends from the housing through an exit aperture;
   a drive that acts upon the syringe to advance it from its refracted position to its extended position and discharge its contents through the discharge nozzle;
   a removable cap adapted to be connected to the housing for closing the exit aperture; and
   a syringe carrier for carrying the syringe as it is advanced, wherein the syringe carrier comprises a sheath for surrounding the reservoir portion of the syringe, wherein the sheath has a first internal diameter along its length, and an intermediate section with a second internal diameter which is smaller than the first internal diameter so that the first end of the sheath is adapted to support the syringe between the reservoir portion and the discharge nozzle;
   wherein the removable cap is adapted to prevent movement of the syringe carrier in a direction towards the exit aperture when the removable cap is connected to the housing and the cap provides a first interface for preventing movement of the syringe carrier in a direction towards the exit aperture and the syringe carrier provides a second interface for directly contacting the first interface, wherein the first interface is located at an edge of a component within the cap, the component is adapted to extend into the exit aperture when connected to the housing and to grip a removable shield on the discharge nozzle of the syringe, and wherein the second interface is located on an annular protrusion at a first end of the syringe carrier which extends over the discharge nozzle.

2. An injection device according to claim 1, wherein the first interface and second interface each comprise a planar surface.

3. An injection device according to claim 1, wherein the annular protrusion is a split annular protrusion.

4. An injection device according to claim 3, further comprising:
   a sliding sleeve projecting from the exit aperture; and
   at least one locking arm which is engageable with the split annular protrusion, wherein the at least one locking arm disengages from the split annular protrusion on movement of the sliding sleeve into the injection device.

5. The injection device of claim 4, wherein the annular protrusion is split on diametrically opposing sides of the protrusion, and wherein each split in the protrusion comprises a locking surface for contacting with a corresponding locking arm.

6. An injection device according to any one of claims 1 to 5 further comprising means for biasing the syringe from its extended position to its retracted position.

7. An injection device according to claim 6, further comprising a support for carrying the means for biasing the syringe.

8. An injection device according to claim 1, wherein the component is an annular component.

* * * * *